(12) United States Patent
Pettit

(10) Patent No.: US 8,707,797 B2
(45) Date of Patent: Apr. 29, 2014

(54) FATIGUE AND/OR CRACK GROWTH TEST SAMPLE

(71) Applicant: Richard G. Pettit, Fruit Heights, UT (US)

(72) Inventor: Richard G. Pettit, Fruit Heights, UT (US)

(73) Assignee: FractureLab, LLC, Fruit Heights, UT (US)

( * ) Notice: Subject to any disclaimer, the term of this patent is extended or adjusted under 35 U.S.C. 154(b) by 35 days.

(21) Appl. No.: 13/768,980

(22) Filed: Feb. 15, 2013

(65) Prior Publication Data
US 2013/0152697 A1 Jun. 20, 2013

Related U.S. Application Data

(62) Division of application No. 13/031,410, filed on Feb. 21, 2011, now Pat. No. 8,544,338.

(51) Int. Cl.
*G01N 3/32* (2006.01)

(52) U.S. Cl.
USPC .............................. 73/808; 73/856

(58) Field of Classification Search
USPC .................... 73/760, 808, 855–866
See application file for complete search history.

(56) References Cited

U.S. PATENT DOCUMENTS

| | | | |
|---|---|---|---|
| 4,116,049 A | 9/1978 | Barker | |
| 4,142,402 A * | 3/1979 | Mattioli et al. | 73/61.62 |
| 4,307,610 A | 12/1981 | Leupp | |
| 4,748,854 A | 6/1988 | Rao | |
| 5,431,062 A * | 7/1995 | Baratta | 73/856 |
| 5,585,570 A * | 12/1996 | Raymond | 73/851 |
| 6,020,674 A | 2/2000 | Zhang et al. | |
| 6,023,980 A | 2/2000 | Owen et al. | |
| 6,339,966 B1 * | 1/2002 | Kalidindi | 73/864.31 |
| 6,417,601 B1 | 7/2002 | Kim | |
| 6,617,766 B1 | 9/2003 | Stoecklein et al. | |
| 7,145,340 B2 * | 12/2006 | Rindlisbacher et al. | 324/321 |
| 7,740,597 B2 * | 6/2010 | Cicenas et al. | 600/566 |
| 7,770,464 B2 | 8/2010 | Meltz et al. | |
| 2002/0019636 A1 * | 2/2002 | Ogilvie et al. | 606/75 |
| 2007/0193757 A1 | 8/2007 | Bar-Cohen et al. | |

FOREIGN PATENT DOCUMENTS

| | | |
|---|---|---|
| DE | 2829858 | 1/1985 |
| GB | 2060179 | 9/1980 |

OTHER PUBLICATIONS

ASTM Standard E466-07, "Standard Practice for Conducting Force Controlled Constant Amplitude Axial Fatigue Tests of Metallic Materials," ASTM International, West Conshohocken, PA, 2007, DOI: 10.1520/E0466-07, www.astm.org. Relevance: Shows standard practice for fatigue tests of general interest and background.

(Continued)

*Primary Examiner* — Max Noori

(57) ABSTRACT

A sample for fatigue and/or crack growth testing, including an axisymmetric or cylindrical gage section with a concentric hole running from a first end, and terminating within the gage section, with one mode of loading introduced at the terminus of the hole, and reacted at the end where the hole originates. A second mode of loading is optionally introduced at a second end of the specimen. Use of the specimen is described in both in the context of an apparatus for fatigue/crack growth testing described in the referenced parent application, as well as with conventional test machines.

9 Claims, 4 Drawing Sheets

(56) References Cited

OTHER PUBLICATIONS

ASTM Standard E647-08e1, "Standard Test Method for Measurement of Fatigue Crack Growth Rates," ASTM International, West Conshohocken, PA, 2008, DOI: 10.1520/E0647-08E01, www.astm.org. Relevance: Shows current practice for crack growth tests. Common test specimens see pp. 699, 703, 707.
Paul C. Paris, Claude Bathias, "Gigacycle Fatigue in Mechanical Practice", CRC Press, 2004, crcpress.com, ISBN: 978-0-8247-2313-2, pp. 51-87. Relevance: Chapter 3 describes ultrasonic piezoelectric dynamic test machine referred to in specification.
H. Tada, P. Paris, G. Irwin, "The Stress Analysis of Cracks Handbook", 3rd Ed., ASME Press, New York, NY, 2000 (completed in 1997, published/copyright in 2000), pp. 55, 58, 61, 62, 390, 395, 406, 410, 412, 429. Relevance: Shows examples of crack/specimen geometries/stress intensit solutions potentially applicable to crack growth testing, including some with circular crack fronts (no free surface effects). p. 429 (fiber pullout problem, as in a fibrous composite) is probably closest to the geometry of the preferred specimen.
Piezo Nano Positioning 2009, Physik Instumente (PI) GmbH & Co. KG product catalogue, Karisruhe/Palmbach (www.pi-usa.us) 2009, pp. 2-192, 2-216. Relevance: Describes well-known mounting & hangling guidelines for protecting/isolating piezoelectric components.
http://www.mts.com/ucm/groups/public/documents/library/dev_002041.pdf A brochure from MTS describing a relatively new high-frequency servohydraulic test machine that would compete with the current invention, but is based on an advanced servo-hydraulic valve technology. The current invention is well suited to reduced scale and cost and is a much less complicated device to maintain. This was not mentioned in the patent (or fully known at the time it was written).

\* cited by examiner

FATIGUE AND/OR CRACK GROWTH TEST SAMPLE

CROSS-REFERENCE TO RELATED APPLICATIONS

This is a division of application Ser. No. 13/031,410 filed 2011 Feb. 21 now U.S. Pat. No. 8,544,338, granted Oct. 1, 2013.

BACKGROUND OF THE INVENTION

1. Field of the Invention

The invention pertains to an novel sample configuration for performing fatigue and/or crack growth tests including complex loading with regard to the relative magnitude and waveform of the load cycles, with the ability to apply axial tension, compression, and/or torsional loading independently, potentially resulting in fully mixed-mode crack growth with non-proportional loading. While resonant (dynamic) conditions may be possible to achieve with the sample, an important object of the invention is to extend the advantages of closed-loop, non-dynamic testing to moderately high frequency ranges. Another object associated with crack growth applications is to provide a crack growth test option with a uniform constraint and/or plasticity-induced closure state across the crack front. Further objects include the ability to configure such a specimen with a stress-intensity that reduces as the crack length increases during a constant load or constant load amplitude test, and to achieve a well-defined, stable crack shape during crack growth. These and other objects, advantages and characteristic features of the present invention will become more apparent upon consideration of the following description thereof when taken in connection with the accompanying drawings depicting the same.

2. Description of the Prior Art

Fatigue and/or crack growth testing is necessary in many engineering applications where component durability and safety concerns merit the associated costs. For cyclic testing, it is often desirable to increase the frequency of such testing to more closely simulate field conditions, as is particularly true for high-cycle fatigue or crack growth threshold testing. Nevertheless, high frequency testing is also desirable if for no other reason than to reduce the duration and cost of testing. The most common fatigue test machines apply cyclic load to a sample mounted between two connection points with cyclic loading supplied by servohydraulic, or servoelectric actuation systems, and seldom exceed 100 Hz frequency capability due to inherent design limitations. However, it is not uncommon for these machines to employ closed loop load, displacement, or even crack tip stress-intensity control capable of arbitrary load waveforms and complex loading sequences, which can be very desirable in some applications. The use of these types of machines and the common samples employed for fatigue and crack growth testing are described by ASTM standards (especially ASTM E466 and E647) and is well known to those familiar with the art.

Application Ser. No. 13/031,410 pertaining to a device for cyclic loading of a test sample, is related to the present application as referenced above, and provides an extensive description of prior art test devices relevant to achieving higher test frequencies. While these devices are not specifically relevant to the present application for a test sample, it is largely true for cyclic loading devices that the higher the stiffness of the sample, the higher the possible operation frequency, particularly for non-resonant conditions involving closed-loop, arbitrary waveform operation. While treatment of the stiffness of the test machine and its elements is not uncommon in the art, the stiffness of the specimen is a less common design object. The specimen configuration associated with an ultrasonic piezoelectric dynamic system operating at 15-30 MHz as described in *Gigacycle Fatigue in Mechanical Practice*, by Paul C. Paris and Claude Bathias CRC Press 2004, is one exception, associated with a specific resonant testing system, and resembling a common "dogbone" style specimen.

With regard to prior art in sample geometries for fatigue and crack growth testing, the most commonly used configurations are described in the ASTM standards referenced previously, with several other potential test configurations described in stress intensity handbooks such as the *Stress Analysis of Cracks Handbook*, $3^{rd}$ Ed (H. Tada et al, ASME press, 1997). The compact tension specimen is of particularly common usage for crack growth, but is well known to have reduced constraint in the vicinity of the intersection between the crack front and the free surface, resulting in non-uniform plasticity induced closure across the crack front for cyclic applications. Specimens with quarter circular or semicircular cracks are also popular, and have the benefit of resembling common naturally occurring crack shapes, but are also subject to free surface effects, though to a lesser degree. Free surface effects are absent in samples with a fully circular crack front, such as circular cylindrical or tubular specimens with a circumferential crack loaded in tension. However, because the stress intensity increases with crack length for these configurations (for a given load), any deviation from a truly concentric crack front creates an uneven stress intensity, with the highest stress intensity where the local crack length is longest. Thus the crack shape tends to become more irregular as the crack grows, resulting in crack front shape instability. This hampers correlation of the data with a single standard stress intensity solution, and impairs the reproducibility of results. The short rod chevron notched specimen described in U.S. Pat. No. 4,116,049, is one of the few specimens known to have a reducing stress intensity solution, which is advantageous for its use as a fracture toughness specimen, but the shape of the crack front, which is generally assumed to be straight for analysis purposes typically exhibits significant curvature. In fact, nearly all commonly used crack growth sample configurations exhibit crack shapes that typically differ from those assumed in the stress intensity solutions, introducing a degree of error in the interpretation of the results. This deficiency is not easily corrected merely by a more careful analysis of the specimen, because it is linked to free surface effects and can be material dependent.

SUMMARY OF THE INVENTION

The invention pertains to a sample, or specimen for performing fatigue and/or crack growth tests, that is suitable for testing in various loading devices found in the art, but which is particularly well suited for testing in a device for applying cyclic loads which is the topic of application Ser. No. 13/031, 410 referenced above, and which will be used as an exemplary context for the description of the features and benefits of the sample. In order to offer high frequency cyclic capability, the test device employs at least one actuator based on a solid state material system which undergoes deformations in response to the application of energy, such as a piezoceramic material operating under cyclic electrical input. Such materials can be oriented and energized in such a manner as to produce axial or shear (torsional) deflections, but generally are capable of relatively small strains for use in actuation. In order to enable high-load/high-frequency operation without the limitations associated with resonant operation, the full load range provided to the specimen must be supplied by the actuator (without dynamic amplification). This requires that the total load train including the test device and the sample connected together must be as stiff as is practical to maximize the load capability for a given actuator. This also allows the apparatus to retain the capability to perform more conventional low frequency testing where that is a requirement.

Additionally, solid state actuators are typically weak in tension, but testing in tension is a common necessity. Thus the test sample of the present invention, in embodiments that involve axial actuation, is naturally configured so that when operated with the device of referenced application Ser. No. 13/031,410, an axial compression load in the actuator results in an axial load of the desired sign in the specimen, even if the specimen is to be loaded in tension. Further, protective compressive preloading is applied to the axial actuators by preloading the specimen directly (in tension) without any parasitic load being diverted to a separate prestressing member, nor is any such member in the tensile load path to reduce the load train stiffness. This also enables the practical application of a substantial amount of preload, enabling the use of bipolar excitation of the actuator, which increases the load range capability.

For a single loading mode, such as axial loading, the device of referenced application Ser. No. 13/031,410 includes two load frames, an internal load frame substantially enclosed by a first external load frame, with at least one guiding interface between them to maintain a substantially concentric and coaxial alignment during operation. This arrangement provides the stiffest practical means to transmit a load from an axially deflecting actuator system to a sample and back again, completing a load circuit. The sample is connected to a first end of the internal load frame and first end of the first external load frame, forming a first load path from the internal load frame through the sample to the external load frame. Cyclic loads are transmitted to the sample from the actuator or system of actuators which extends along the axis between a second end of the internal load frame and a second end of the external load frame, imparting cyclic load via the first load path through the sample.

It should be noted that the use of the word "end" herein should not be strictly limited to denote only the very extreme extent of the opposite sides of a component in the strictest sense, but in a more general sense wherein the two ends denote two regions of a component substantially including the opposing extremities with an intermediate region between. Reference to interfaces or connections at the ends so described presupposes suitable interfacing features or means of attachment.

The guiding interface spoken of may be embodied as a region of direct contact between adjacent load frames, or indirectly as an interface between one of the load frames and the sample, which is rigidly attached to the other load frame, or both, so long as the alignment of all members of the load frames is substantially maintained thereby during operation.

The load frames, though described as a single component, may consist of multiple members, jointed by force of direct contact or other means suitable for the type of load being transferred. The load frames may include sensing hardware, such as a load cell for instrumentation purposes.

As mentioned before, it is desirable to prestress the actuators in compression, particularly axial actuators, both to protect the actuator from damage, and also to facilitate the running of tests with a high mean load, and potentially to take advantage of the increased load range and actuator durability achievable by bipolar operation for some actuator types. Preloading is achieved with the sample mounted by providing an adjustable length connection at some point within the first external load frame or its connection either to the actuator or the sample, by which the complete load train representing the device and the specimen can be tightened to put axial actuators in compression when in the neutral state (power off). Care should be taken in the design of the adjustable length connection to make it sufficiently stiff. For example, if a threaded connection is used, the optional addition of a locknut will result in a stiffer connection, improving the load capability of the machine. Similar measures should also be considered at any other detachable connections in the device.

For axial loading, the sign of the loading is defined herein by the sign of the loading in the first internal load frame, which is typically the same as the sign of the predominate stress in the specimen. To run the device in tension, the actuator must be oriented so that when it is in compression, the first internal load frame is in tension. The actuator and first external load frames experience stress of opposite sign in this preferred arrangement.

For a device configured for axial tension loading, the internal load frame experiences stress substantially of the opposite sign from the first external load frame, and is thus in compression, like the actuator. To avoid torsional or bending loads in the actuator as a protective measure, the internal load frame, or the first external load frame adjacent to the attachment to the actuator at its second end, may preferably include two members, which transfer load by direct contact between a locally spherical convex surface in one member, and a either a flat surface, or preferably a matching concave spherical surface in the other member. The interface between matching spherical surfaces is preferred for most applications because it provides a stiffer connection axially than a spherical/flat interface. The amount of torsional load transferred by friction can be kept small by limiting the diameter of the contact area. This may be particularly useful if the adjustable length connection described above for prestressing the actuator is a threaded connection.

To enhance the stiffness of the apparatus, it is beneficial to utilize high modulus materials in the load frames, such as a form of tungsten carbide, which can exhibit an elastic modulus up to 90,000 ksi or higher. For elevated temperature testing, it is required to insert the mounted sample into a furnace during operation. To avoid overheating of the actuators or load cells one or more members of the various load frames may consist of a material of low thermal conductivity. Zirconia ceramic, which has low thermal conductivity, but also high strength and high elastic modulus (about 30,000 ksi), is particularly well suited for this purpose.

Active cooling may also be necessary both to alleviate furnace heat or heat generated within the actuators during operation. This can be accomplished by utilizing cooling passages through the load frames, and especially in gaps left for this purpose between adjacent load frames, or between actuators and load frames, thus allowing these members to serve as cooling channels as well as structural members.

As mentioned above, instead of a single actuator, actuator systems may be driven by more complex actuation systems. Novel concepts for high stroke actuation systems combining the strokes of more than one actuator in an actuation system will be described in the detailed description of the preferred embodiments.

Because of the high stiffness of the test device described, and the availability of rapid response solid state energy conversion materials, and piezoceramics in particular, it is estimated that the device could be operated at frequencies up to 2000 Hz with sufficiently powerful electronics, active cooling, and with a sufficiently stiff specimen.

The performance of the test device is dependent to a large degree on the stiffness of the specimen. While the machine can be configured to test various specimens, a description of the novel specimen concept which constitutes the invention claimed herein now follows. This new specimen geometry consists of a length of the material to be tested, with a first and second end, of axisymmetric and preferably circular cylindrical shape on the exterior over at least a portion of its length, wherein a substantially circular hole extends from the first end of the sample along its longitudinal axis to a depth such that its terminus lies in the midst of the axisymmetric and preferably cylindrically shaped portion. The shape of the hole in the region of its terminus acts as a notch to initiate and grow cracks in the specimen when cyclically loaded by at least two means, a first means introducing load in the vicinity of the terminus of the hole, and a second means introducing load at or near the first end of the sample, distributing load in a substantially axisymmetric manner around the sample axis, such as by a threaded connection, or by the means of a an axisymmetric retaining flange at the first end of the sample. An extension of the internal load frame is guided into the hole, is preferably held in alignment thereby, and interfaces with the hole in the vicinity of its terminus preferably by direct contact between substantially matching flat, spherical, or conical surfaces for the purpose of applying load directed along the axis of the sample.

This sample and loading concept is very stiff, and is well suited to high frequency operation in a test device such as that described herein.

Of particular interest for fatigue crack growth testing is a sample configuration as described above, but more specifically comprising a flat bottomed hole with substantially sharp corners and an internal load frame extension with a matching flat, substantially sharp cornered interface. This configuration, when tested under cyclic loading, typically results in an annular crack emanating from the corner of the flat bottomed hole. If the ratio between the hole diameter and exterior sample diameter in the vicinity of the hole terminus is kept below about 0.6, the stress intensity factor at the crack tip for a constant (or constant amplitude cyclic) load will reduce as the crack grows, promoting stable concentric crack growth. Further, this natural tendency to shed stress intensity as the crack grows is advantageous in some test circumstances. For example, a crack growing in a specimen tested at constant load amplitude will tend to slow as it grows, potentially arresting as it approaches the crack growth threshold. Most conventional specimens have a stress intensity that increases as the crack grows, typically requiring carefully controlled load shedding to obtain threshold results. Also, the full circular crack front exhibits uniform constraint, and thus a uniform plasticity-induced closure state for cyclic loading, making it of special interest for the study of crack growth.

Based on the above discussion, samples with diameter ratios less than 0.6 may be preferred for crack growth tests when a reducing stress intensity profile is advantageous for the test objective. Otherwise, conditions specific to the test objectives may influence one familiar with the art to choose different diameter ratios or other configurations. Stress intensity and stress concentration factors required with regard to the use of a given configuration in testing can be determined using finite-element or boundary element methods common to the art.

An optional second independent mode of operation, such as torsional loading, may be added to the test device described previously by the inclusion of a second external load frame, substantially enclosing the interior and first external load frames over at least a portion of their combined length, and with at least one guiding interface between the first and second external load frames (acting directly or indirectly through the sample) to maintain concentric and coaxial alignment therewith. This second external load frame also connects to the sample to create a load path from the second load frame, through the sample, to the first external load frame. Cyclic loads are transmitted thereby to the sample from a second solid state actuator or system of actuators which extends between the second end of the first external load frame and the second end of the second external load frame. This actuator system includes a solid state energy conversion material oriented and energized so as to produce deflections in the direction of the desired loading corresponding to the mode of operation, preferably compression, or torsional loading.

The independent load frame arrangement inherently separates actuation systems of different modes of operation so that they do not fall directly in each other's load train, avoiding the loss of stiffness that would otherwise occur. For embodiments with both axial and torsional modes of operation, however, it is also necessary to further isolate the load trains so that actuation in one mode will not load the actuator corresponding to the other mode, as a protective measure, since the actuators are typically weak with regard to loads in anything but the direction of actuation. If the two modes of operation are chosen to be tensile and torsional as described in the foregoing, isolation of the torsional stage can be achieved by introducing the torsion through a member that is stiff with regard to torsional displacement, but flexible with regard to axial displacement, such as a thin plate or a leaf spring. The protection measures for the axial stage have already been discussed. Depending on the application, other means of isolation may also be chosen by one skilled in the art.

Novel concepts for high stroke torsional actuation systems combining the strokes of more than one actuator in an actuation system will be described in the detailed description of the preferred embodiments.

When using the preferred sample with a two-stage test device with the second mode of operation being compression or shear, the compressive or torsional load is introduced at a third location at or near the second end of the specimen (beyond the terminus of the hole).

Lastly, it is also possible to configure mounting hardware to enable testing of the preferred sample geometry in prior art servoelectric, servohydraulic, or other types of machines, albeit subject to the limitations of those machines. Examples of these embodiments will be described in more detail hereafter.

BRIEF DESCRIPTION OF THE DRAWINGS

The invention is described by way of example with reference to embodiments that are illustrated in the figures, but without thereby restricting the general object of the invention. In these figures.

DESCRIPTION OF THE PREFERRED EMBODIMENTS

Figure 1:
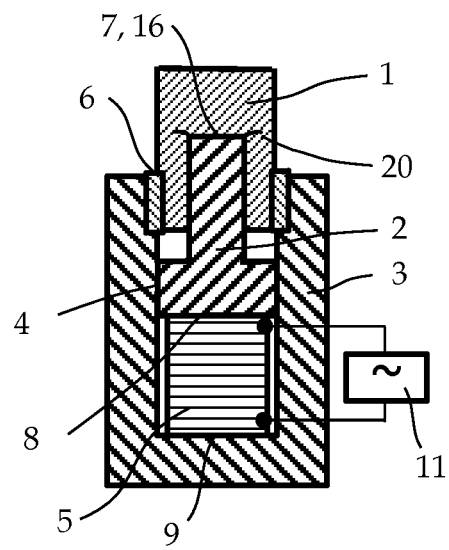
FIG. 1 shows a schematic representation of the design of a fatigue crack growth test apparatus with a single mode of operation including both the device for applying cyclic loads and a sample configured for crack growth testing.
Figure 2:
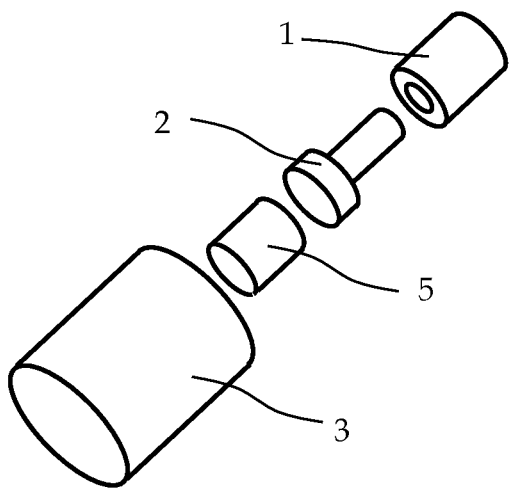
FIG. 2 shows an exploded view of the apparatus in FIG. 1, but without the schematic representation of the power source.

FIGS. 1 and 2 show a schematic representation of an apparatus for performing fatigue or fatigue crack growth testing, including a sample 1 to be tested and a device for applying cyclic loads thereto. The cyclic loading device illustrated includes an internal load frame 2 and a first external load frame 3, each having a first end and a second end, The first external load frame 3 substantially encloses the internal load frame 2 over a portion of its length, and creates a guiding interface 4 therewith to maintain a substantially concentric coaxial alignment between the load frames. The sample 1 having two ends and a bore hole originating in the first end can be attached by way of two substantially rigid detachable connecting interfaces 6, 7 to the first ends of the first external load frame 3 and internal load frame 2, respectively, forming a load path through the sample, by which cyclic loads are transmitted through the sample to the first external load frame 3 from the adjacent load frame 2. The loads originate from an actuator (or actuator system) 5 which extends from the second end 9 of the first external load frame 3 to the second end 8 of the adjacent load frame 2, so as to impart cyclic loading via the load path through the sample 1. The actuator 5 includes a solid state material system which undergoes deformations in response to the application of energy, with the orientation of the solid state actuation material and the application of energy such that the deformations occur predominantly in the direction of the desired loading. For the purposes of illustration, it is assumed that the solid state actuator 5 includes a preferably piezoceramic material configured to deflect with either an angular or preferably axial displacement with the application of electricity from the cyclic power source 11. FIG. 1 also shows a preferred arrangement of the actuator such that the predominant orientation of stress in the actuator material due to an imposed deflection is of opposite sign to the orientation of the stress in the first external load frame, thereby loading the specimen in tension, when the actuator is loaded in compression. An adjustable length connection (not explicitly shown, but possibly integrated into the connecting interface 6), allows the assembly to be tightened together to place the actuator in compression in its neutral state.

Figure 3:
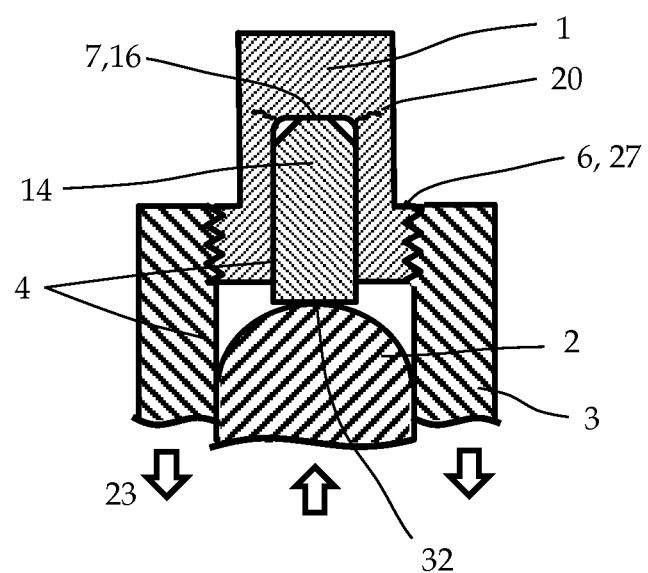
FIG. 3 shows an enlarged view of a sample configured for axial fatigue testing mounted with an exemplary threaded attachment configuration on a device otherwise identical to FIG. 1.

FIG. 3 illustrates the use of a threaded connection interface 6 between the first end of the first exterior load frame 3 and the first end of the sample 1, suitable for reacting the preferred (tensile) axial loads 23 shown for illustration. The threaded arrangement also allows adjustment of the length of the total load train created by the sample 1 and the load frames 2 and 3, allowing the actuator (not shown in FIG. 3) to be preloaded in compression in the neutral state. FIG. 3 further illustrates a multi-component internal load frame wherein the sample 1 engages an internal load frame extension 14 and wherein the internal load frame extension contacts the primary internal load frame 2 with a spherical/flat interface 32. The spherical/flat interface 32 between internal load frame components protects the axial actuator (not shown in FIG. 3) from potentially damaging torsional loading resulting from the tightening of the threaded connection, as well as any loads arising from misalignment.

Figure 4:
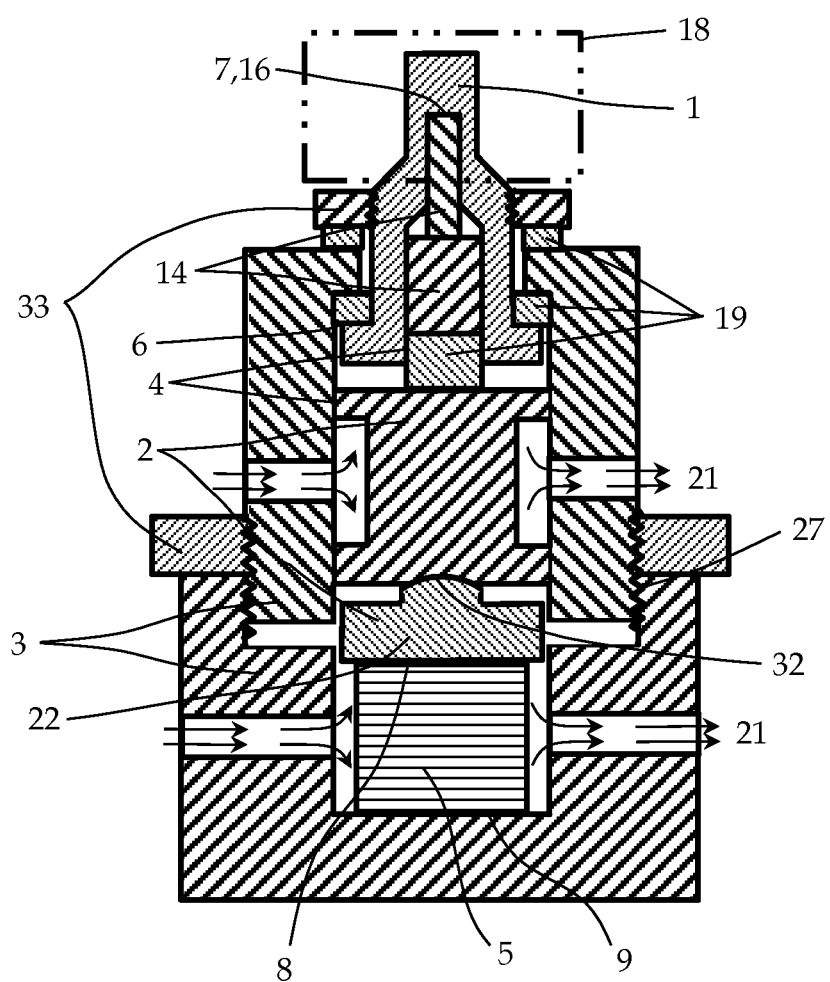
FIG. 4 shows a schematic representation of a fatigue crack growth test apparatus with a multi-part first external load frame, further configured for high temperature testing.

FIG. 4 shows a version configuration of the apparatus configured for elevated temperature testing with axial tension loading, including various enhancements. Enhancements in this illustration include an elongated sample 1, further additional components in the internal load frame, and a multi-part first external load frame. For illustration purposes, the configuration of the sample 1 has been extended to protrude into a furnace or other heat source 18, and illustrates the use of a flanged interface connection 6. A load cell 22 for test instrumentation is included as a member of the internal load frame 2. For illustration purposes a button type load cell 22 with a convex spherical interface is depicted, mating with a concave surface in the adjacent member of the internal load frame 2. This interface provides improved stiffness compared to the sphere-to-flat-interface of FIG. 3, but remains flexible with regard to bending and torsion, adjusting for small amounts of misalignment and protecting against torsional preloading induced during tightening of an adjustable length connection 27, also shown to preload the load axial actuator 5 in compression. As an option to provide additional stiffness, locknuts 33 are shown securing the adjustable length connection 27, and the specimen connection interface 6. The load cell 22 and the actuator 5 are located away from the heat source 18 as a protective measure, to avoid overheating these potentially heat sensitive components. As a further protection, insulating members 19 are included in the external load frame 3, and between the internal load frame 2 and the internal load frame extension 14. These insulating members require a combination of low thermal conductivity and high modulus and strength, thus a zirconia ceramic is preferably used. As a further protection against heat from the both the heat source 18 as well as from internal heating within the solid state actuator 5, air or another cooling medium is circulated along paths 21 in channels or gaps between the adjacent load frames 2 and 3, and/or between actuator 5 and load frame 3.

In any embodiment, but particularly in elevated temperature applications, the compliance of the overall load train potentially limits the loads that can be applied for a given actuation system. It is thus advantageous to employ high modulus materials, such as a tungsten carbide, in the load frames 2, 3 and any connecting hardware, especially in the most compliant members, such as members of the internal load frame extension 14.

Because of the high stiffness of the cyclic test device described, and the availability of rapid response solid state energy conversion materials, and piezoceramics in particular, it is anticipated that the device could be operated in closed loop mode at frequencies up to 2000 Hz with sufficiently powerful electronics, active cooling, and with a sufficiently stiff sample, such as will now be described.

The preferred sample 1 illustrated in FIGS. 1-3, consists of a length of the material to be tested, of circular axisymmetric shape generally, and a preferably cylindrical shape on the exterior over at least a portion of its length, wherein a substantially circular hole extends from the center of a first end of the sample, along its longitudinal axis to a depth such that its terminus 16 lies in the midst of the said axisymmetric and preferably cylindrically shaped portion, the shape of the hole in the region of its terminus 16 acting as a notch to initiate and grow a crack 20 in the sample 1 when subjected to cyclic loading. The configuration shown in FIG. 1, with a sharp-cornered flat bottomed terminus 16 and matching loading interface 7, is well suited for fatigue crack growth testing. In FIG. 3, the more rounded terminus 16 is more suited to fatigue/crack initiation testing. Note also that the means of connection between the first end of the internal load frame 2 and the terminus 16 in FIG. 3 includes a separate internal load frame extension 14 which makes a guiding interface 4 within the sample to maintain a concentric and coaxial alignment with the sample.

Many variants on the shape of the hole terminus 16 and the interface with either the internal load frame 2 or the internal load frame extension 14 can be made by one familiar with the art to best serve the objectives of the testing, including, but not limited to configurations where load is transferred by way of substantially matching flat, spherical, or conical surfaces.

As explained previously, for applications wherein the test objective is best met with a stress intensity factor that reduces naturally as the crack grows, the preferred sample configurations 1 may be advantageously configured to have an interior to exterior diameter ratio below 0.6 in the section proximate to the hole terminus 16.

Figure 5:
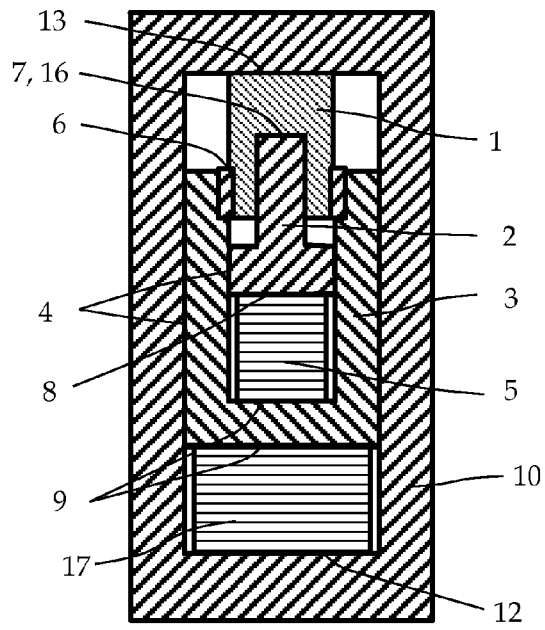
FIG. 5 shows a schematic representation of a fatigue crack growth test apparatus with independent axial tension and compression loading capability.
Figure 6:
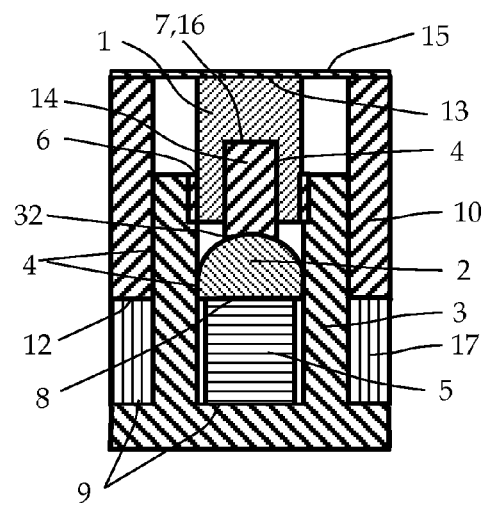
FIG. 6 shows a schematic representation of a fatigue crack growth test apparatus with independent axial tension and torsion loading capability.

FIGS. 5 and 6 show schematic representations of embodiments that include an optional second external load frame 10 to introduce a second mode of operation. The second external load frame 10 substantially encloses other load frames 2, 3 over at least a portion of their combined length, making a guiding interface 4 with the adjacent load frame 3, thereby maintaining a concentric and coaxial arrangement between the various load frames 2, 3, and 10. In each illustration, the actuator 5 extending between the internal load frame 2 and first external load frame 3 provides tensile loading of the sample. An additional actuator 17 extending between the first and second external load frames 3, 10 is configured to provide compressive loading in FIG. 5, and torsional loading in FIG. 6. An embodiment of the preferred specimen is also shown wherein additional mode of loading is transferred by way of a third connecting interface 13 at the second end of the sample 1. Many of the enhancements shown in prior figures are excluded here for simplicity of illustration, but could be similarly applicable.

FIG. 6 also shows two isolating features necessary to isolate the axial actuator 5 and torsional actuator 17 stages including a spherical contact surface interface 32 to protect the axial actuator 5 from torsion, and an axially flexible member 15, such as a thin plate or a leaf spring, that protects the torsional actuator 17 from axial tension, but is sufficiently stiff to transfer torsional loads. The torsional actuator 17 is shown to be of tubular geometry for illustration purposes, but could also be of other configurations.

Figure 7:
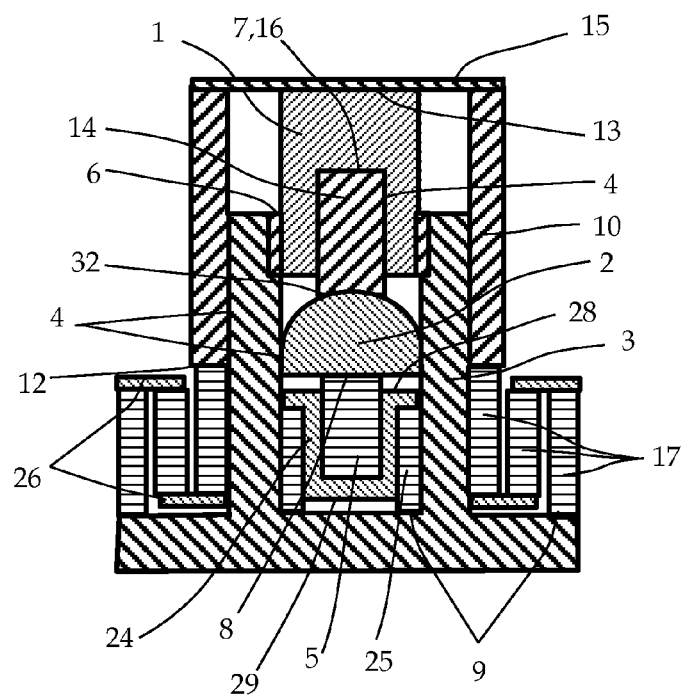
FIG. 7 shows a schematic representation of a fatigue crack growth test apparatus with independent axial tension and torsion loading capability illustrating high-deflection solid state actuation system configurations for each mode.

FIG. 7 shows an enhanced tension/torsion concept illustrating multiple actuator actuation systems for tension and torsion that are designed to provide increased deflection over single actuator systems. The axial actuation system shown has two actuators 5 and 25, but will be described in terms of its general form, which utilizes at least two axial actuators, including one solid cylindrical actuator 5, and at least one tubular actuator 25, wherein the actuators are nested coaxially in a substantially concentric manner, held in place by a single intermediate member 24 with a first and second end, and wherein the odd member(s) 5 (numbered from the center outward) are inserted into at least one recess in the intermediate member 24 open to the first end 28, and the even actuator(s) 25 are inserted into the at least one recess in the intermediate member 24 open to the second end 29. The free ends of the actuators protrude from each end 28, 29 of the intermediate member and connect to the second ends of the internal and first external load frames. Inversion of the actuator system relative to the position shown is equally acceptable.

The torsional actuation system concept, which is shown with three tubular actuators 17 in FIG. 7, in general has a plurality of tubular torsional actuators 17 nested concentrically wherein the adjacent actuators are configured to produce rotational deflections of opposite sign for a signal of a given polarity, and are joined by annular ties 26 in a zigzag cross-sectional pattern wherein each tie 26 joins a pair of adjacent actuators 17, with the tie 26 located at the end of the assembly corresponding to the sign of the deflection of the outermost actuator of the pair, and wherein the free ends of the innermost and outermost actuators are connected to the second ends of the adjacent load frames at points 9 and 12. The particular sign convention (right hand or left hand) used in the arrangement is not critical but will determine the sign of the resultant deflection.

Lastly, an example will be given of sample mounting hardware to enable testing of the preferred sample in conventional prior art load frames, though the use of such an arrangement will be subject to the limits of the particular machine used, with regard to test frequency, etc.

Figure 8:
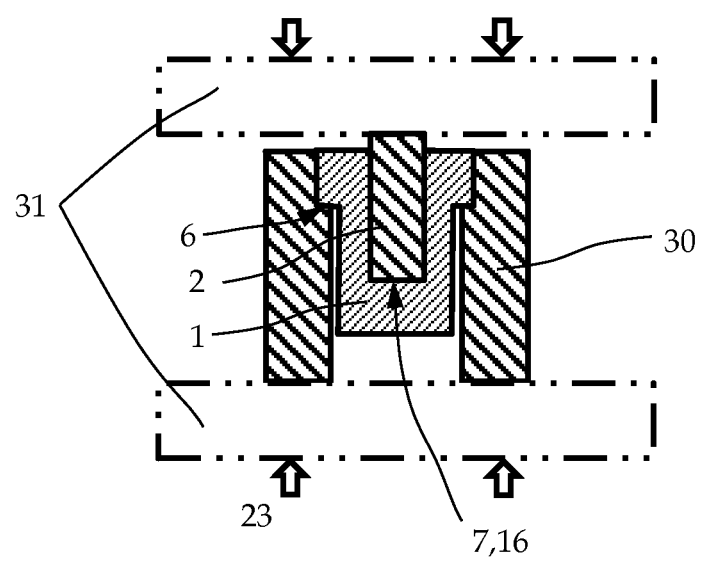
FIG. 8 illustrates connecting hardware to mount the preferred specimen in a conventional test machine configured with loading platens.

FIG. 8 shows an example of mounting hardware to permit loading the preferred sample geometry in a conventional (servohydraulic, servoelectric, etc) test machine. For illustration purposes, it is assumed that the prior art test machine is configured with two parallel loading plates 31 for cyclic compression loading 23, but the desired test state in the sample is tension. This is accomplished by use of an internal load frame 2 similar to the load frame extension described previously, but connecting with one of the load plates 31 by direct contact. While the direct contact connection with the loading plates 31 is shown between two flat surfaces, the internal load frame may alternately have a spherical contact surface, to allow for misalignment. An external load frame extension 30 is also utilized, substantially enclosing the sample over at least a portion of its length, and extending from a connection interface 6 between the first end of the sample 1 and the first end of the external load frame 30, to a flat-to flat connection with the second load plate 31 at the second end of the external load frame extension.

Although the present invention has been described in considerable detail with reference to certain preferred versions thereof, other connection methods for different specimen geometries or different test machine configurations can be easily devised by one skilled in the art. Therefore, the spirit and scope of the appended claims should not be limited to the description of the preferred versions contained herein. The reader's attention is directed to all papers and documents which are filed concurrently with this specification and which are open to public inspection with this specification, and the contents of all such papers and documents are incorporated herein by reference. All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

LIST OF REFERENCE SYMBOLS

1 Sample
2 Internal load frame
3 First external load frame

4 Guiding interface
5 Solid state actuator/actuation system acting between internal and first external load frames
6 Connecting interface at first end of first external load frame or external load extension
7 Connecting interface at first end of internal load frame
8 Connecting interface at second end of internal load frame
9 Connecting interface at second end of first external load frame
10 Second external load frame
11 Power source
12 Connecting interface at second end of second external load frame
13 Connecting interface at first end of second external load frame
14 Internal load frame extension
15 Isolating member to protect torsional actuator(s) from axial loads
16 Terminus of loading hole in sample
17 Solid state actuator/actuation system acting between first external and second external load frames
18 Furnace/heat source to heat sample for elevated temperature testing
19 Insulating members
20 Crack growing in specimen
21 Active cooling fluid flow
22 Load cell
23 Loads assumed for purpose of illustration
24 Intermediate member
25 Tubular axial actuator
26 Annular connecting tie
27 Adjustable length connection
28 First end of actuator system
29 Second end of actuator system
30 External load frame extension
31 Loading platens from prior art test machine
32 Direct contact interface between a convex spherical surface in a first member and a flat or matching concave spherical surface in a second member
33 Locknut

The invention claimed is:

1. A sample for fatigue and crack growth testing, comprising:
   (a) a length of the material to be tested comprising:
      (i) a first and second end; and
      (ii) an axisymmetric shape on the exterior over at least a portion of its length; and
   (b) a substantially circular hole extending from the first end of the sample along its longitudinal axis to a depth such that its terminus lies in the midst of the said axisymmetrically shaped portion, wherein:
      (i) the hole is concentric with said axisymmetric portion; and
      (ii) the hole has a constant diameter along at least a portion of its length in the vicinity of the terminus; and
      (iii) the region of the terminus of the hole forms a notched shape to initiate and/or grow cracks in the specimen under cyclic loading; and
   (c) at least two means of contacting a test machine capable of transmitting loads, wherein:
      (i) a first means introduces load in the vicinity of the terminus of the hole; and
      (ii) a second means introduces load at or near the first end of the sample, distributing load in a substantially axisymmetric manner around the sample axis.

2. The sample according to claim 1, wherein the said first means of contact to a test machine comprises an internal load frame, with at least one member, that extends into the hole, guided by sliding contact within the hole to form a substantially concentric and coaxial alignment between the hole and the internal load frame, and interfacing with the hole in the vicinity of its terminus by direct contact between substantially matching flat, spherical, or conical surfaces for the purpose of applying said load in a direction along the axis of the sample.

3. The sample according to claim 2, wherein the substantially matching flat, spherical, or conical surface for the purpose of axial load introduction comprise a flat bottomed, circular hole terminus with substantially sharp corners and a substantially matching flat-ended internal load frame extension with substantially sharp corners.

4. The sample according to claim 1 wherein:
   (a) the said axisymmetric portion includes a circular cylindrical shape over a portion of its length; and
   (b) the said terminus of the hole lies within the said cylindrical portion.

5. The sample according to claim 4, wherein the ratio of the said hole diameter to the said outer diameter of the sample in the vicinity of the hole terminus is less than 0.6.

6. The sample according to claim 1, wherein the said second means of contact to a test machine includes a threaded connection, or a flange extending radially outward from said first end of the sample, or a combination thereof.

7. The sample according to claim 1 further comprising a third means of contact at the second end of the sample for introduction of compression or torsional loads.

8. A means for mounting the sample according to claim 2 within a conventional load frame configured with two parallel plates for compressive loading, wherein the said internal load frame extension protrudes from the said first end of the sample and interfaces by a direct contact connection to one of the loading plates; and further comprising:
   (a) an external load frame extension with a first and second end, substantially enclosing the sample over at least a portion of its length; comprising:
      (i) means for connecting the first end of the sample to the first end of the external load frame extension, such as by a threaded or flanged interface; and
      (ii) a flat-to-flat direct contact connection between the second end of the external load frame extension with the second loading plate.

9. A method of axial cyclic testing the sample of claim 1 comprising the steps of:
   (a) mounting the sample between two load frames,
   (b) connecting the load frames to a solid state actuator system, with the actuator arrangement such that the specimen is substantially loaded in tension when the actuator system is in compression,
   (c) tightening a variable length connection in a load train consisting of the specimen, actuator system, and load frames connected together until a desired preload is met, with the actuator system in compression,
   (d) cyclically energizing the solid state actuator system to create a cyclic load in the sample.

* * * * *